(12) United States Patent
Omura et al.

(10) Patent No.: US 6,512,008 B1
(45) Date of Patent: Jan. 28, 2003

(54) SUBSTANCE WK-5344A AND WK-5344B AND PROCESS FOR PRODUCING THE SAME

(75) Inventors: Satoshi Omura, Tokyo (JP); Hiroshi Tomoda, Tokyo (JP); Yoko Takahashi, Tokyo (JP)

(73) Assignee: Kitasato Institute, Tokyo (JP)

( * ) Notice: Subject to any disclaimer, the term of this patent is extended or adjusted under 35 U.S.C. 154(b) by 0 days.

(21) Appl. No.: 09/857,268

(22) PCT Filed: Mar. 8, 1999

(86) PCT No.: PCT/JP99/01101

§ 371 (c)(1),
(2), (4) Date: Aug. 22, 2001

(87) PCT Pub. No.: WO00/53792

PCT Pub. Date: Sep. 14, 2000

(51) Int. Cl.$^7$ .......................... C12P 17/18; C12P 13/00; C12N 1/20; A01N 55/02; A61K 31/295

(52) U.S. Cl. ................. 514/502; 435/118; 435/128; 435/253.5

(58) Field of Search ................. 435/128, 118, 435/253.5; 514/502, 185, 410

(56) References Cited

PUBLICATIONS

K. Hiroaki et al., "Purification, Microheterogneity, and Stability of Human Lipid Transfer Perotein" *Journal of Biological Chemistry*, vol. 264, No. 7, Mar. 5, 1989, pp 4082–4087.

A. Endo, "Compactin (ML–236B) and Related Compounds as Potential Cholesterol–Lowering Agents that Inhibit HMG–CoA Redutase" *Journal of Medicinal Chemistry*, vol. 28, No. 4, 1985, pp 401–405.

A. Endo, "The Discovery ND Development of HMG–CoA Reductase Inhibitors" *Journal of Lipid Research*, vol. 33, 1992, pp 1569–1582.

*Primary Examiner*—Herbert J. Lilling
(74) *Attorney, Agent, or Firm*—Young & Thompson (57) ABSTRACT

The present invention relates to novel substance having inhibitory action on cholesteryl ester transfer protein, WK-5344A substance and WK-5344B substance, and process for production thereof. A microorganism belonging to genus Streptomyces having ability to produce WK-5344A substance and WK-5344B substance is cultured in a medium, and the WK-5344A substance and the WK-5344B substance are accumulated in the medium, then the WK-5344A substance and the WK-5344B substance are isolated from the said medium. Since the present substance shows significant inhibitory action on cholesteryl ester transfer protein, the substance is effective for prevention and treatment of diseases caused by accumulation of cholesterol in human.

5 Claims, 8 Drawing Sheets

SUBSTANCE WK-5344A AND WK-5344B AND PROCESS FOR PRODUCING THE SAME

BACKGROUND OF THE INVENTION

1. Field of the Invention

The present invention relates to WK-5344A substance and WK-5344B substance and production thereof. More particularly, the present invention pertains novel substances, WK-5344A substance and WK-5344B substance having inhibitory action for cholesteryl ester transfer protein and production thereof.

2. Description of Related Art

Various preventive medicaments for myocardial infarction and cerebral accident due to accumulation of cholesterol in vascular wall such as arteriosclerosis caused by adult hypertension have been known. These include, for example, pravastatin, mevinolin and fluvastatin (Endo, A. Journal of Medicinal Chemistry 28, 401–405, 1985 and Endo, A. Journal of Lipid Research 33, 1569–1582, 1992).

Onset of myocardial infarction and cerebral accident and the process of these diseases are very complicate and complex. Consequently, substances having different mechanism of action for treatment of these diseases have been strongly required.

Recently, as a result of westernization of the daily life for foodstuffs, cause of death due to myocardial infarction and cerebral accident as a result of accumulation of cholesterol in the vascular wall is increased and is problem of the life-style related diseases. Most cholesterol is mainly esterified in liver and intestine by long chain fatty acids to form cholesteryl esters, which are secreted into blood as components of chylomicron and very low density lipoprotein, and are circulated in blood mainly as components of low density lipoprotein and high density lipoprotein.

Low density lipoprotein, which transfers cholesterol supplied from the liver into the peripheral tissues, is a risk factor for stimulating arteriosclerosis. On the contrary, the high density lipoprotein collects the cholesterol from the peripheral tissues and is thought to be a factor for suppressing progress of arteriosclerosis. It is cholesteryl ester transfer protein to be involved in the exchange reaction of cholesteryl ester between both lipoproteins, and that is involved in maturation of low density lipoprotein.

Consequently, a substance, which inhibits function of the cholesteryl ester transfer protein, develops decrease of low density lipoprotein, the risk factor for arteriosclerosis, in the blood, and, contrary to that, develops anti-arteriosclerotic action as a result of increase in the high density lipoprotein, which suppresses arteriosclerosis, and is effective for these diseases.

SUMMARY AND OBJECT OF THE INVENTION

We have studied metabolic product of microorganisms isolated from soils in order to find out novel bioactive substances, and found that cultured mass of newly isolated microbial strain WK-5344 from soil produced substances having inhibitory action on cholesteryl ester transfer protein. As a result of isolation and purification of said cholesteryl ester transfer protein inhibitor from said cultured mass, since such substances having such the chemical structures have not been known, we have designated these substances as WK-5344A substance and WK-5344B substance.

The present invention has been completed accordingly to such knowledge.

Further object of the present invention is to provide a process for production of WK-5344A substance and WK-5344B substance or salt thereof comprising culturing a microorganism belonging to genus Streptomyces and having ability to produce WK-5344A substance and WK-5344B substance, accumulating WK-5344A substance and WK-5344B substance in a cultured mass and isolating WK-5344A substance and WK-5344B substance from said cultured mass.

DESCRIPTION OF THE PREFERRED EMBODIMENTS

According to the preferred embodiment of the present invention, the present invention pertains the process for production of novel substance, WK-5344A substance and WK-5344B substance, or salt thereof wherein the microorganism belonging to genus Streptomyces having ability to produce WK-5344A substance and WK-5344B substance is Streptomyces sp. WK-5344. The present invention further relates to a microorganism belonging to genus Streptomyces having ability to produce WK-5344A substance and WK-5344B substance and said microorganism is Streptomyces sp. WK-5344 (FERM BP-6668).

The microorganism having ability to produce WK-5344A substance and WK-5344B substance of the present invention (hereinafter designates as WK-5344 substance producing microorganism) belongs to genus Streptomyces, and is sufficient to have ability to produce WK-5344A substance and WK-5344B substance without no limitation. Example of the preferable microbial strain used to produce WK-5344A substance and WK-5344B substance of the present invention is Streptomyces sp. WK-5344, which is isolated from newly collected soil by the present inventors.

The taxonomical properties of the present strain are as follows.

(I) Morphological Properties

Vegetative mycelia grow well in various agar media and no fragmentation was observed. Aerial mycelia grow abundantly on inorganic salts-starch agar and glycerol-asparagine agar to show white to gray color. In microscopic observation, aerial mycelia showing spiral and chains of more than 20 spores are observed. Form of spores is oval with size of 1.0×0.5 μm. Surface of spore is spiny. No sclerotium, sporangium and zoospore are observed.

(II) Cultural Properties on Various Agar Media

The cultural properties of the present producing strain observed according to the method of E. B. Shirling and D. Gottlieb (International Journal of Systematic Bacteriology, 16, 313, 1966) are shown in Table 1.

Color tones are determined referring to Color Harmony Manual, 4th ED. (Container Corporation of America, Chicago, 1958) as standard color, and are indicated as name of color tone with its cord in parenthesis. The following table indicates, if not specifically defined, results of visual observation of the state of culture of this strain in various culture media at 27° C. for 2 weeks.

TABLE 1

| Sucrose-nitrate agar | |
|---|---|
| growth | good, light mustard tan (2ie) |
| reverse | light mustard tan-moss green (2ie-241g) |
| aerial mycelium | abundant, ashes (5fe) |
| soluble pigment | no production |
| Glucose-asparagine agar (ISP) | |
| growth | good, bamboo (2gc) |
| reverse | bamboo (2gc) |
| aerial mycelium | abundant, alabaster tint-ashes (13ba-5fe) |
| soluble pigment | pastel yellow (1db) |
| Glycerol-asparagine agar (ISP) | |
| growth | good, biscuit (2ec) |
| reverse | bamboo (2gc) |
| aerial mycelium | abundant, alabaster tint-ashes (13ba-5fe) |
| soluble pigment | pastel yellow (1db) |

TABLE 1-continued

Inorganic salts-starch agar (ISP)

| | |
|---|---|
| growth | good, bamboo (2gc) |
| reverse | camel (3ie) |
| aerial mycelium | abundant, ashes (5fe) |
| soluble pigment | no production |

Tyrosine agar (ISP)

| | |
|---|---|
| growth | good, bamboo (2gc) |
| reverse | light mustard tan-moss green (2ie-24lg) |
| aerial mycelium | abundant, alabaster tint (13ba) |
| soluble pigment | no production |

Oatmeal agar (ISP)

| | |
|---|---|
| growth | moderate, bamboo-golden yellow (2fb-2kb) |
| reverse | bamboo-covert brown (2fb-2li) |
| aerial mycelium | moderate, ashes (5fe) |
| soluble pigment | citron (1gc) |

Yeast extract-malt extract agar (ISP)

| | |
|---|---|
| growth | good, bamboo (2gc) |
| reverse | mustard (2le) |
| aerial mycelium | abundant, pearl gray (13cb) |
| soluble pigment | olive yellow (1le) |

Nutrient agar

| | |
|---|---|
| growth | moderate, bamboo (2gc) |
| reverse | nugget gold (2nc) |
| aerial mycelium | moderate, ashes (5fe) |
| soluble pigment | no production |

Peptone-yeast extract-iron agar (ISP)

| | |
|---|---|
| growth | moderate, dull gold (2ng) |
| reverse | light mustard tan (2ie) |
| aerial mycelium | poor, white (a) |
| soluble pigment | no production |

Glucose-nitrate agar (ISP)

| | |
|---|---|
| growth | moderate, light mustard tan (2ie) |
| reverse | mustard (2le) |
| aerial mycelium | moderate, white (a) |
| soluble pigment | gold (1½lc) |

Glycerol calcium-malate agar

| | |
|---|---|
| growth | moderate, bamboo (2gc) |
| reverse | light wheat-bamboo (2ea-2gc) |
| aerial mycelium | abundant, pearl (3ba) |
| soluble pigment | citron (1gc) |

Glucose-peptone agar

| | |
|---|---|
| growth | moderate, bamboo (2gc) |
| reverse | light wheat-golden yellow (2ea-2kb) |
| aerial mycelium | poor, white (a) |
| soluble pigment | no production |

(III) Physiological properties

| | |
|---|---|
| (1) Melanin pigment | |
| (a) Tyrosine agar | negative |
| (b) Peptone-yeast extract-iron agar | negative |
| (c) Glucose-peptone-gelatin medium | negative |
| (d) Tryptone-yeast extract broth | negative |
| (2) Tyrosinase reaction | negative |
| (3) Hydrogen sulfide production | negative |
| (4) Nitrate reduction | positive |
| (5) Gelatin liquefaction (21–23° C.) (Glucose-peptone-gelatin medium) | negative |
| (6) Hydrolysis of starch | positive |
| (7) Coagulation of skim milk (37° C.) | negative |
| (8) Peptonization of skim milk (37° C.) | positive |
| (9) Growth temperature | 9–37° C. |

-continued (III) Physiological properties

| | |
|---|---|
| (10) Utilization of carbon sources (Pridham and Gottlieb medium) Utilized: glucose, arabinose, xylose, melibiose, mannitol, rhamnose, fructose and inositol Slightly utilized: raffinose and sucrose | |
| (11) Decomposition of cellulose | negative |

(IV) Composition of Cell Wall

Diaminopimelic acid of cell wall is LL type.

Taxonomical properties of the present strain are summarized as follows.

Diaminopimelic acid in cell wall is LL type. Vegetative mycelia show good growth on various agar media and no fragmentation was observed. Form of aerial mycelia is spiral with long spore chain. Surface of spore is spiny. Various properties on culture are showing brownish color tone of vegetative mycelia and white to gray color tone of aerial mycelia. Soluble pigment formation is greenish yellow pigment on yeast extract-malt extract agar medium, oatmeal agar medium, glucose-asparagine agar medium, glycerol-asparagine agar medium, glucose-nitrate agar medium and glycerol-calcium malate agar medium.

According to results of these observations, the present strain has been identified as a strain belonging to genus Streptomyces and was referred to Streptomyces sp. WK-5344.

The present strain was deposited in the International Patent Organism Depositary, National Institute of Advanced Industrial Science and Technology, located at AIST Tsukuba Central 6, 1-1, Higashi 1-chome Tsukuba-shi, Ibaraki-ken, 305-8566 Japan, as FERM BP-6668 on Mar. 1, 1999.

Although WK-5344 substance producing microbial strain was explained as a preferable strain of the present invention, taxonomical properties are very easily mutated as general properties of microorganisms and are not stable. It is also well known to mutate by natural mutation technique or commonly performed artificial mutation techniques such as ultraviolet irradiation, X-ray irradiation or applying mutagenic agents such as N-methyl-N'-nitro-N-nitrosoguanidine and ethyl methanesulfonate. Consequently, strains having ability to produce WK-5344 substance belonging to genus Streptomyces including artificial mutants and natural mutants can be used in the present invention. Strains mutated by cell engineering technology such as cell fusion and gene manipulation are included within the WK-5344 substance producing strain.

In production of WK-5344A substance and WK-5344B substance of the present invention, WK-5344 substance producing microorganism belonging to genus Streptomyces is cultured in preferable medium. In the culture of the present microorganism, culture method for common microorganism is generally provided. Examples of media are those nutrient media containing assimilable carbon sources for microorganism, digestible nitrogen sources for microorganism and, if necessary, adding inorganic salts.

Examples of the above assimilable carbon sources are glucose, sucrose, molasses, starch, dextrin, cellulose, glycerol and organic acid, and are used in alone or in combination. Examples of digestible nitrogen sources are organic nitrogen source such as peptone, meat extract, yeast extract, dry yeast, soy bean powder, corn steep liquor, cotton seed oil, casein, soy bean protein hydrolysate, amino acids and urea, and inorganic nitrogen source such as nitrate and ammonium salt, and are used in alone or in combination.

Further, if necessary, inorganic salt such as sodium salt, potassium salt, calcium salt, magnesium salt and phosphate, and heavy metal salt are added. In the medium, trace nitrogen element, growth stimulating substance or precursor for stimulating growth of the present strain and production of WK-5344A substance and WK-5344B substance can be added.

Cultivation can be performed under aerobic condition such as shaking culture or aeration stirring culture. pH of the medium is preferably performed at neutral condition. For idustrial production, submerged aeration is preferable. Culturing condition can be performed within range of 20–37° C., generally at 24–30° C. preferably at 27° C. Culturing time is generally for 2–6 days in the liquid culture to accumulate WK-5344A substance and WK-5344B substance, and the cultivation can be terminated when maximum production of WK-5344A substance and WK-5344B substance can be performed.

The culture condition such as composition of medium, culturing temperature, rate of stirring and aeration volume can be adjusted and selected in order to obtain preferable conditions depending on types of strain used and external conditions. In the liquid culture, if foaming occurs, antifoaming agents such as silicon oil, vegetable oil and surface active agents can be used.

Since WK-5344A substance and WK-5344B substance accumulated in the cultured mass are contained in the cultured liquid or cultured mycelia, the cultured mass is filtered by adding filter aid such as Celite and Hyflosupercell or centrifuged to separate culture liquid and mycelia, which are extracted with organic solvent, then the extracts are advantageously concentrated and isolated WK-5344A substance and WK-5344B substance.

Isolation of WK-5344A substance and WK-5344B substance from the culture filtrate is performed by extracting the culture filtrate with water immiscible organic solvent such as ethyl acetate, butyl acetate and benzene and concentrating the extract in vacuo to obtain WK-5344A substance and WK-5344B substance. Said crude substance can be purified by known method used for purification of lipophilic substance, for example column chromatography using carrier such as silica gel or alumina to obtain purified WK-5344A substance and WK-5344B substance.

In order to isolate WK-5344A substance and WK-5344B substance from mycelia, the mycelia are extracted with aqueous water miscible organic solvent such as aqueous methanol, concentrated the extract in vacuo, extracted the concentrate with water immiscible organic solvent such as ethyl acetate, butyl acetate or benzene, and purified the extract with or without combining the above extract obtained from the culture liquid to obtain WK-5344A substance and WK-5344B substance.

Physico-chemical properties of WK-5344A substance and WK-5344B substance of the present invention are described as follows.

[I] WK-5344A Substance (1) Molecular formula: $C_{45}H_{30}N_3O_{13}Fe$ [in high resolution FAB mass spectrum (positive), m/z 877.1203 (M+H) is measured] (calculated: 877.1206)

(2) Molecular weight: 876 [m/z 877 (M+H)$^+$ and 899 (N+Na)$^+$ are observed by FAB mass spectrum (positive)]

(3) Specific rotation: $[\alpha]_D^{25}$ –3000° (c=0.01, methanol)

Figure 1:
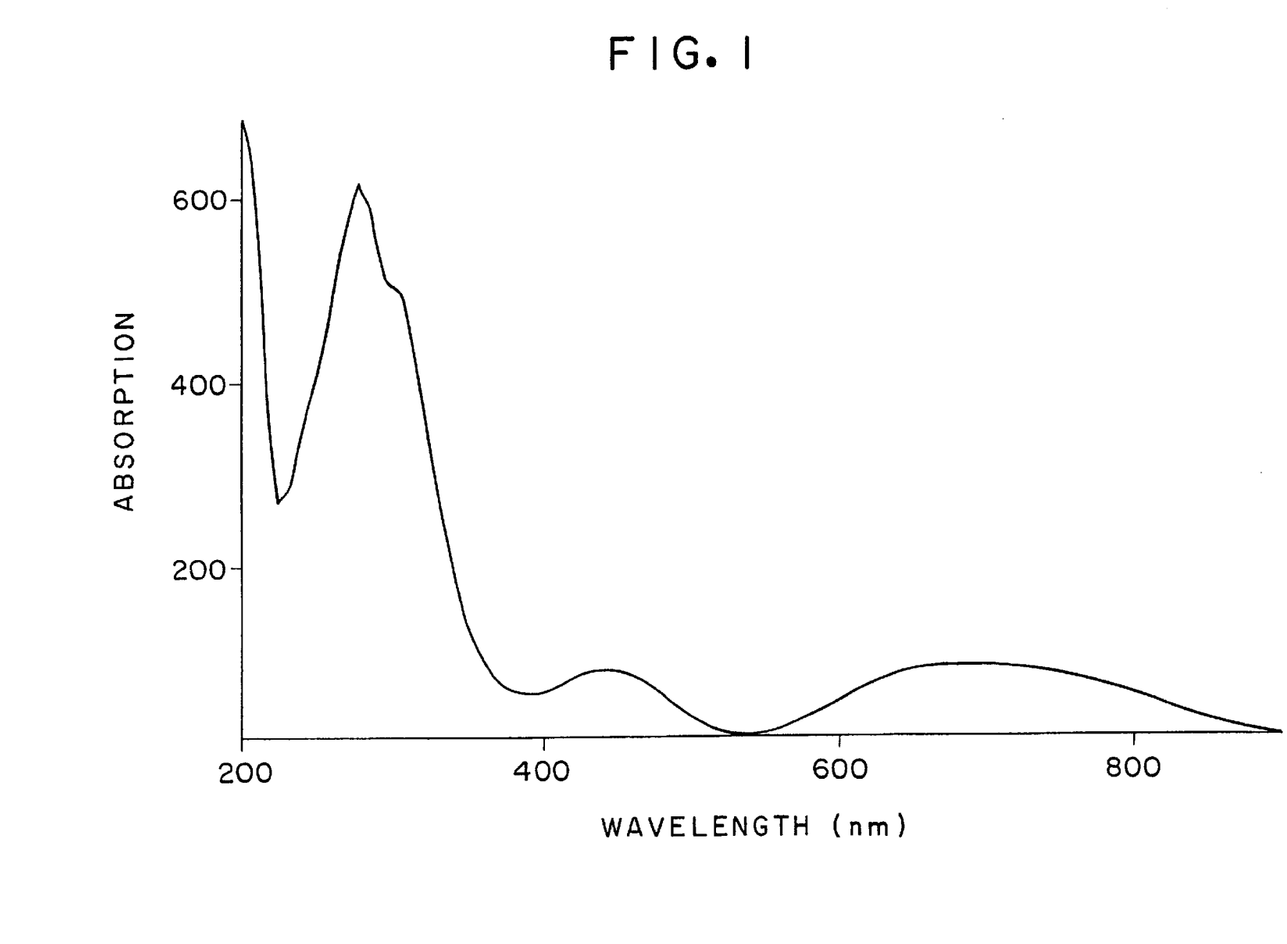
FIG. 1 shows UV spectrum of WK-5344A substance of the present invention (in CH$_3$OH).

(4) UV spectrum: UV spectrum measured in methanol is shown in FIG. 1. Specific maximum peaks are observed at around 280, 305 (shoulder), 440 and 690 nm.

Figure 2:
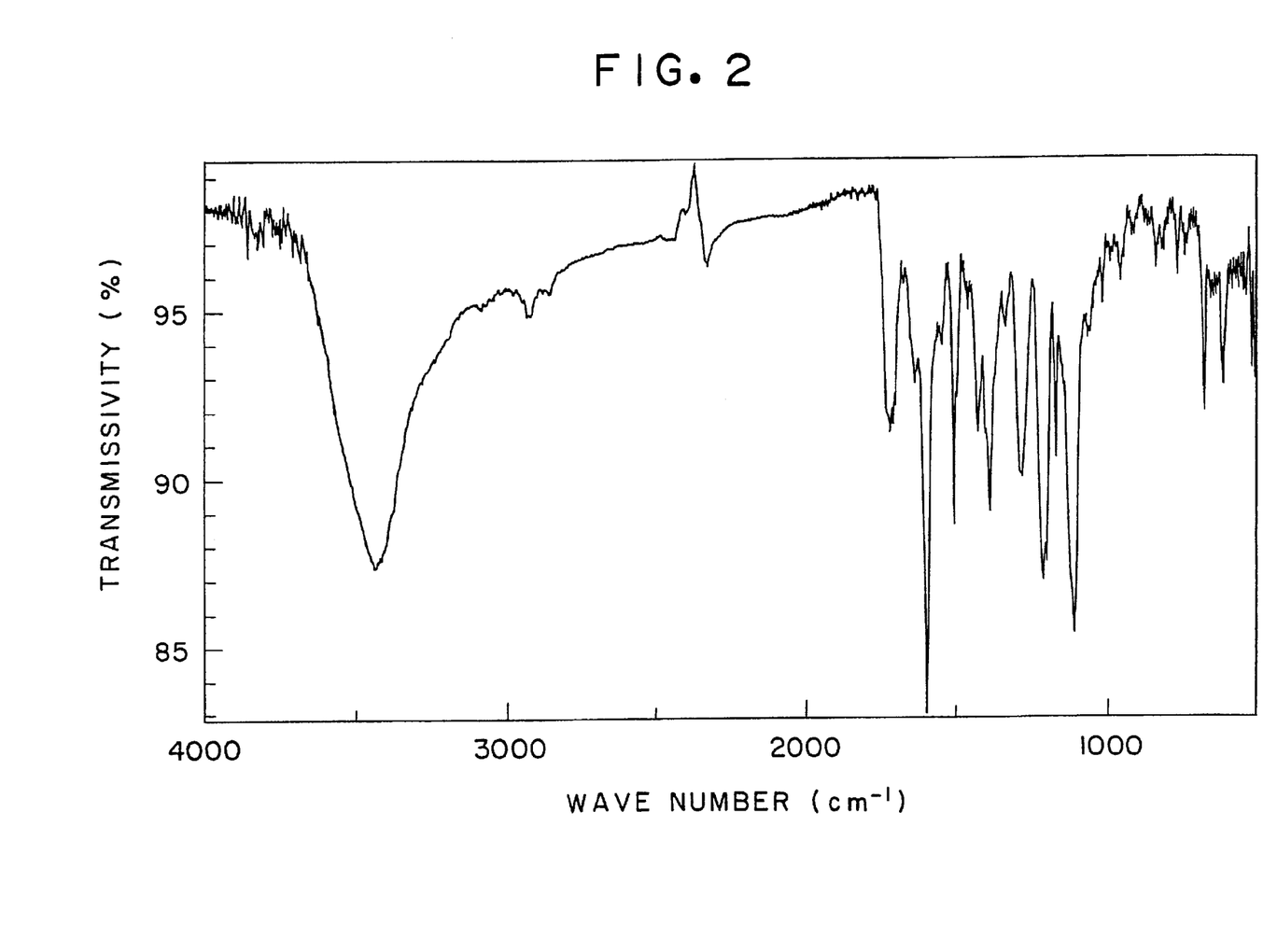
FIG. 2 shows IR spectrum of WK-5344A substance of the present invention (KBr tablet).

(5) IR spectrum: IR spectrum (KBr tablet) is shown in FIG. 2. $\lambda max^{KBr}$ cm$^{-1}$: 3400, 1728, 1701, 1597, 1493, 1385, 1284, 1207 and 1105.

(6) Solubility in solvent: Soluble in methanol, ethanol, acetonitrile, ethyl acetate, chloroform and dimethyl sulfoxide. Insoluble in water.

Figure 3:
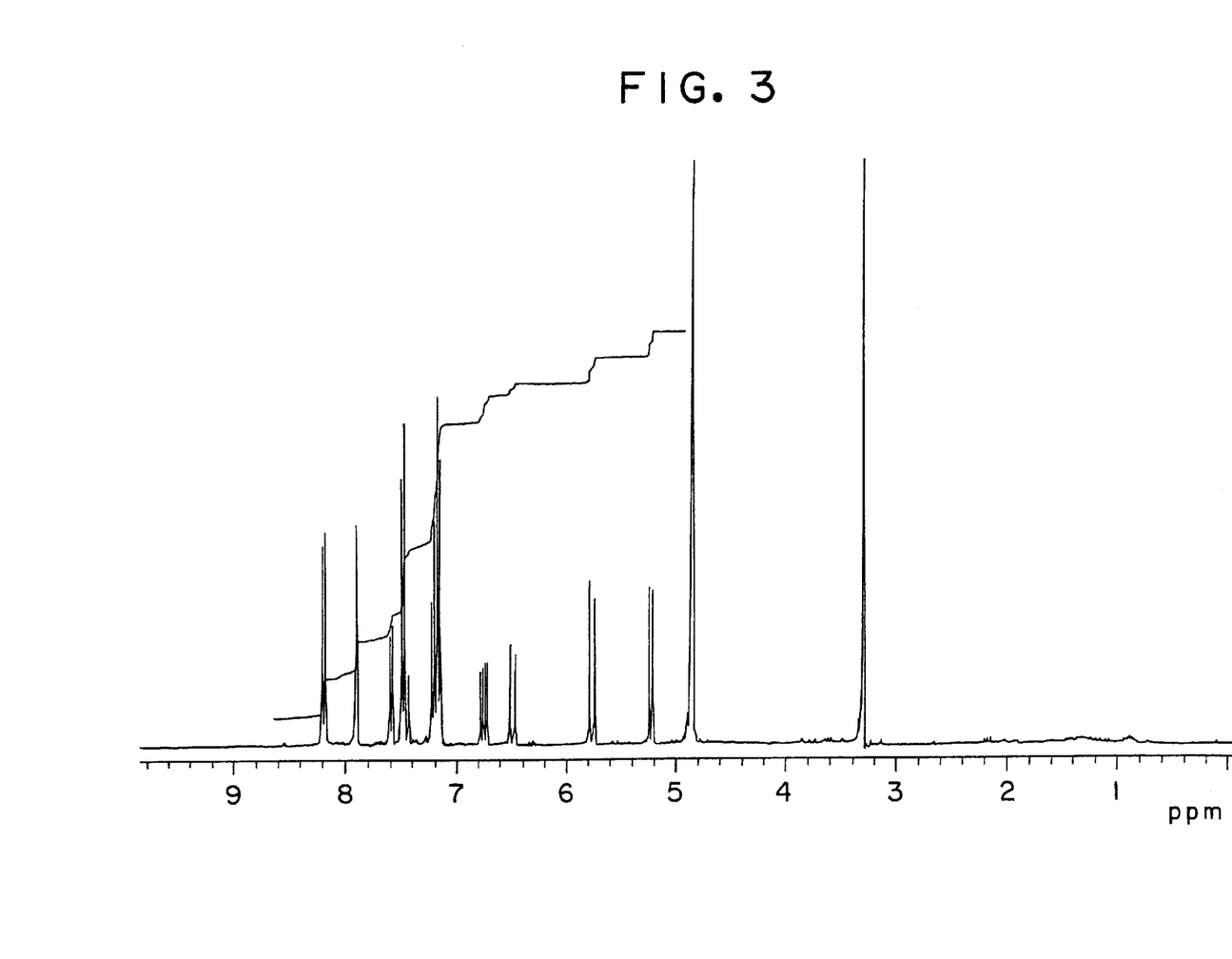
FIG. 3 shows proton NMR spectrum of WK-5344A substance of the present invention (CD$_3$OD).

(7) Nature of substance: neutral (8) Color and form substance: greenish powder (9) Proton NMR: FIG. 3 (Varian NMR, in deuterium methanol, 400 MHz)

Figure 4:
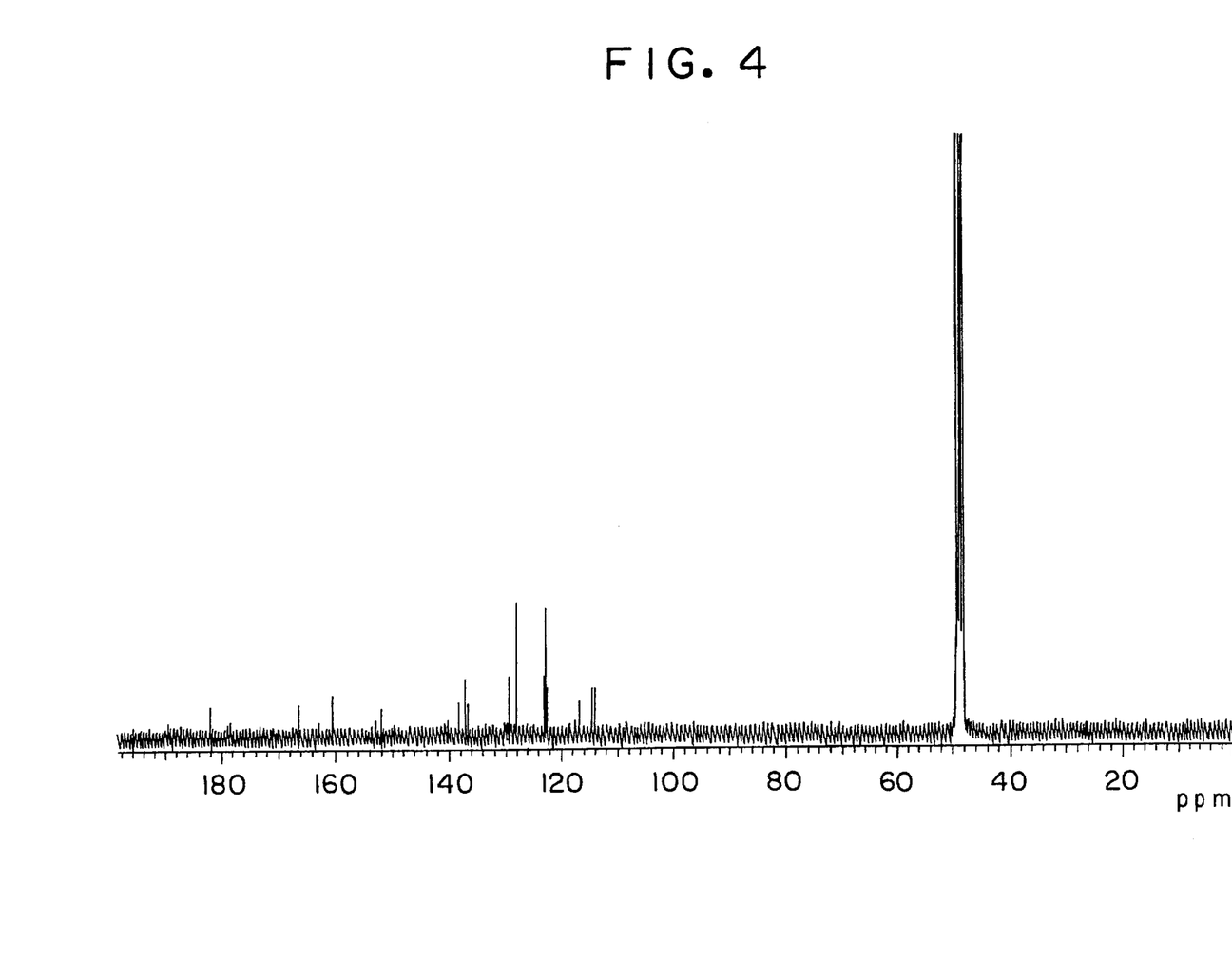
FIG. 4 shows carbon NMR spectrum of WK-5344A substance of the present invention (CD$_3$OD).

(10) Carbon NMR: FIG. 4 (Varian NMR in deuterium methanol, 100 MHz)

Structure of WK-5344A substance was determined by considering the above physico-chemical properties and spectral data as follows.

[II] WK-5344B Substance (1) Molecular formula: $C_{46}H_{30}N_3O_{14}Fe$ [in high resolution FAB mass spectrum (positive), m/z 905.1151 (M+H) is measured] (calculated: 905.1155)

(2) Molecular weight: 904 [m/z 905 (M+H)$^+$ and observed by FAB mass spectrum (positive)]

(3) Specific rotation: $[\alpha]_D^{25}$ –1000° (c=0.01, methanol)

Figure 5:
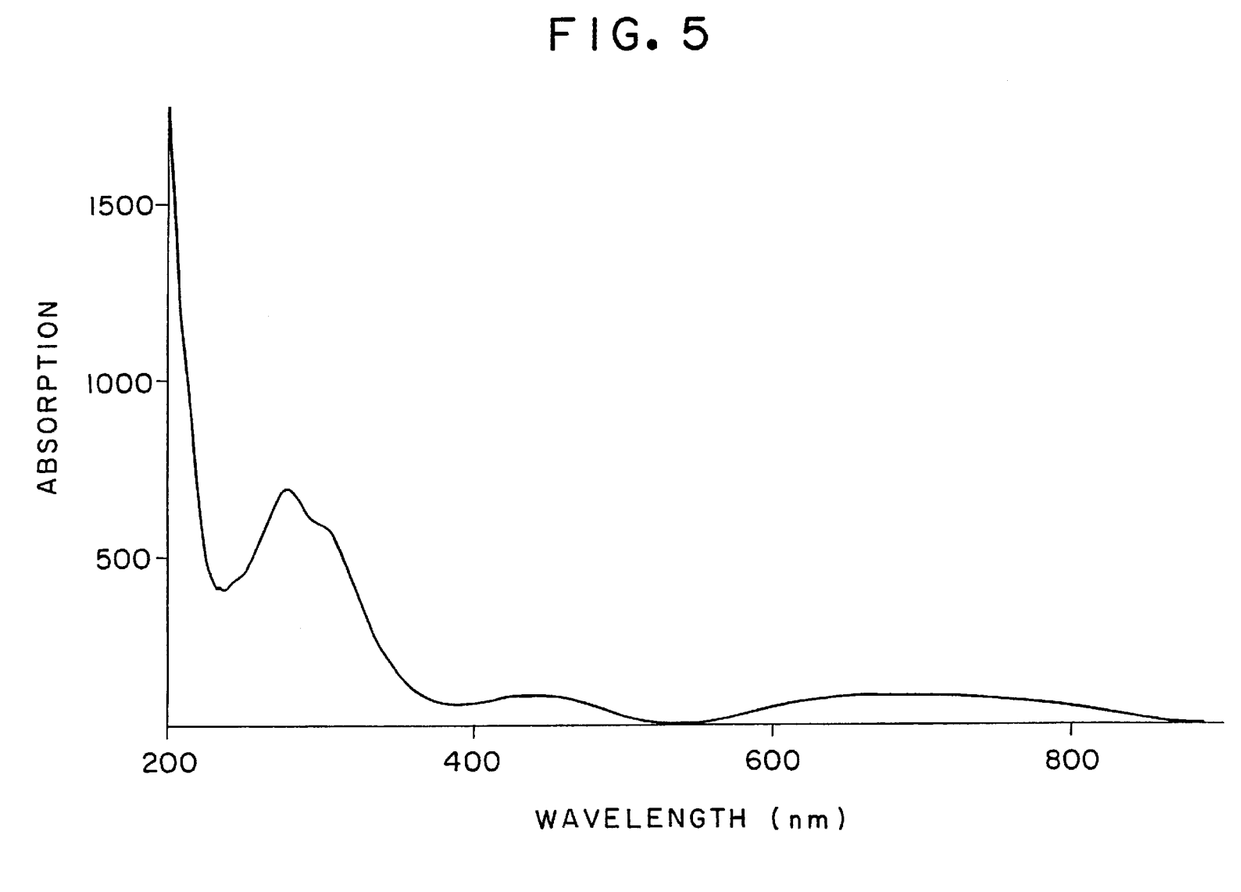
FIG. 5 shows UV spectrum of WK-5344B substance of the present invention (in CH$_3$OH).

(4) UV spectrum: UV spectrum measured in methanol is shown in FIG. 5. Specific maximum peaks are observed at around 285, 303 (shoulder), 445 and 698 nm.

Figure 6:
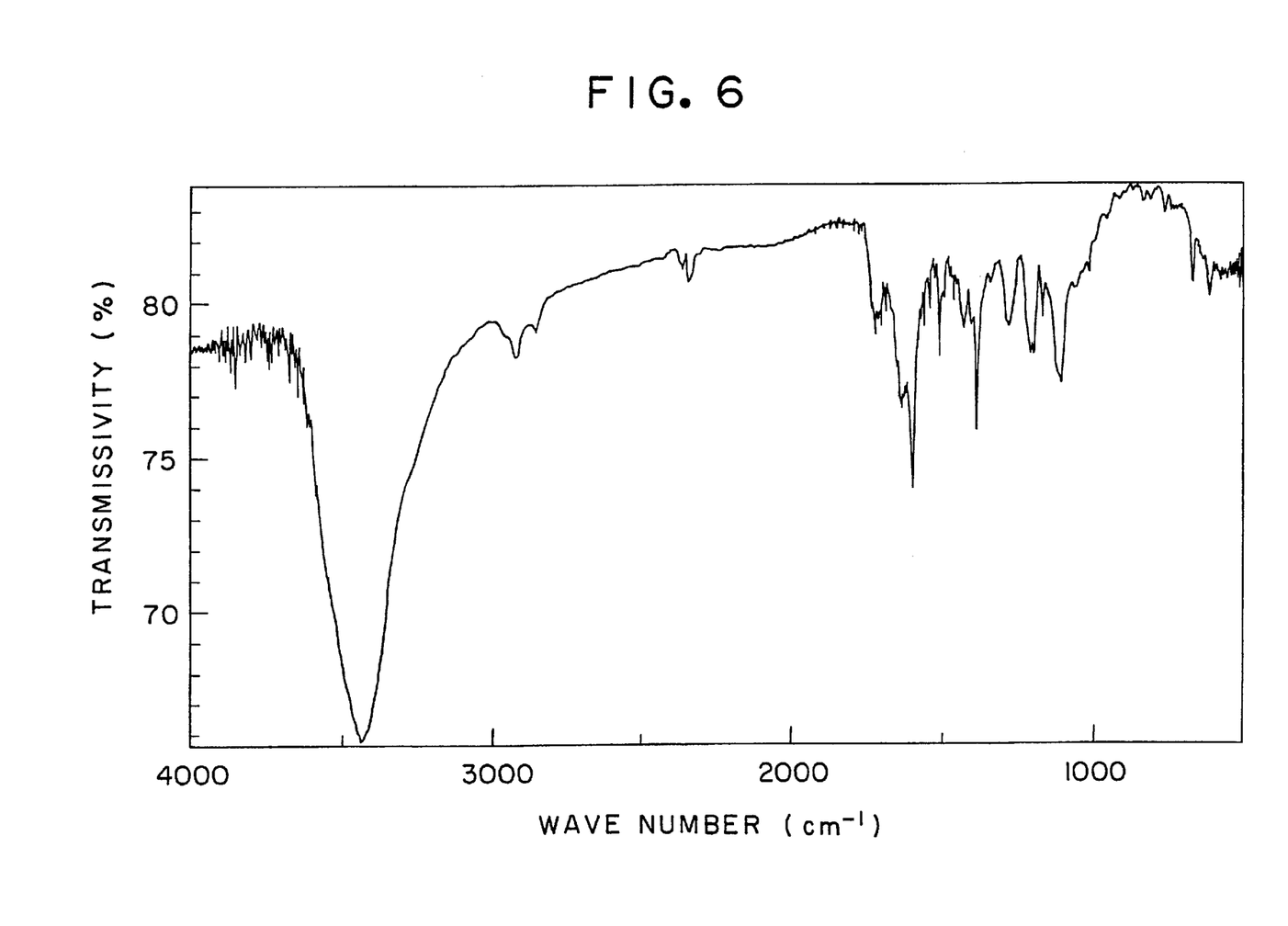
FIG. 6 shows IR spectrum of WK-5344B substance of the present invention (KBr tablet).

(5) IR spectrum: IR spectrum (KBr tablet) is shown in FIG. 6. λmax$^{KBr}$ cm$^{-1}$: 3400, 1718, 1701, 1597, 1508, 1385, 1281, 1196 and 1105.

(6) Solubility in solvent: Soluble in methanol, ethanol, acetonitrile, ethyl acetate, chloroform and dimethyl sulfoxide. Insoluble in water (7) Nature of substance: neutral (8) Color and form of substance: greenish powder

Figure 7:
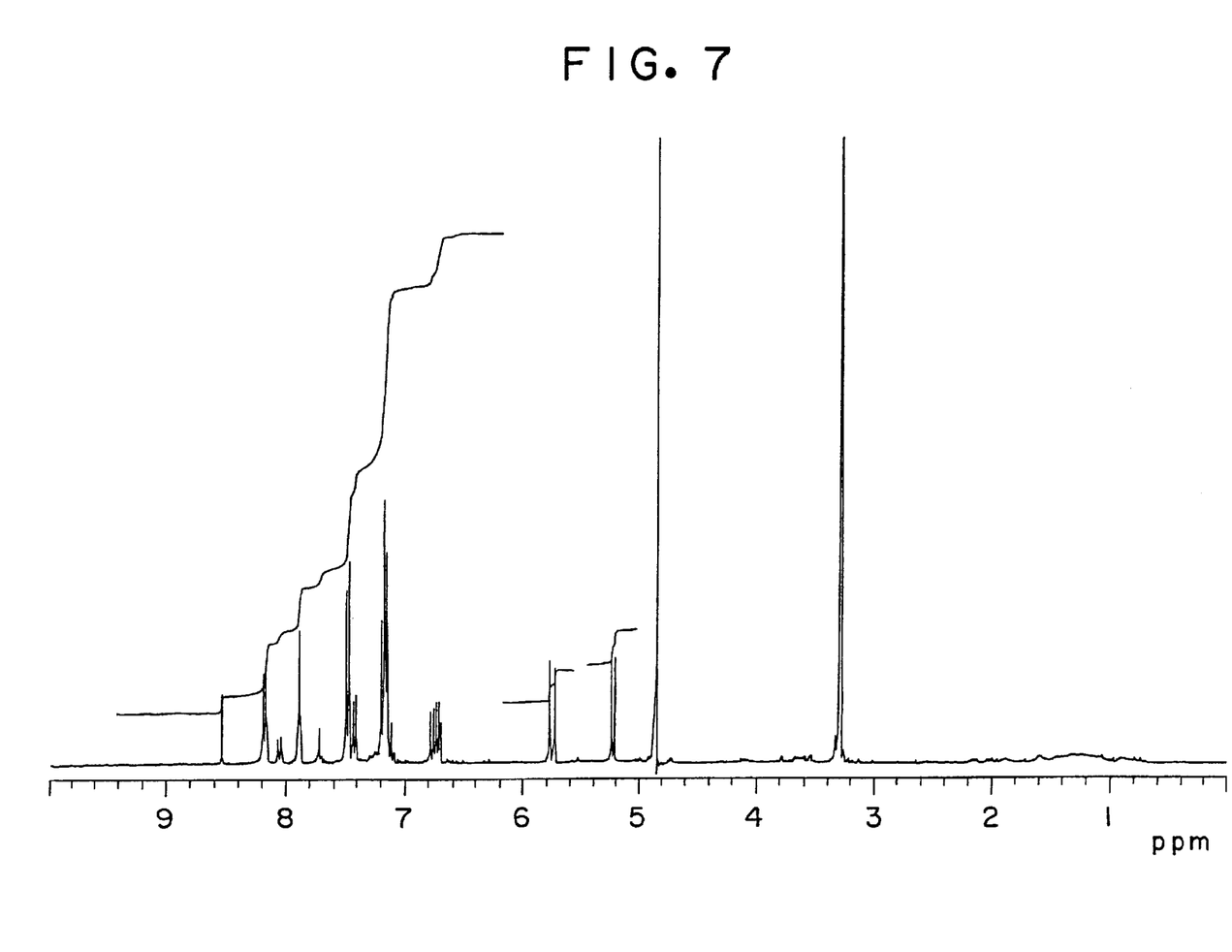
FIG. 7 shows proton NMR spectrum of WK-5344B substance of the present invention (CD$_3$OD).

(9) Proton NMR: FIG. 7 (Varian NMR, in dueterium methanol, 400 MHz)

Figure 8:
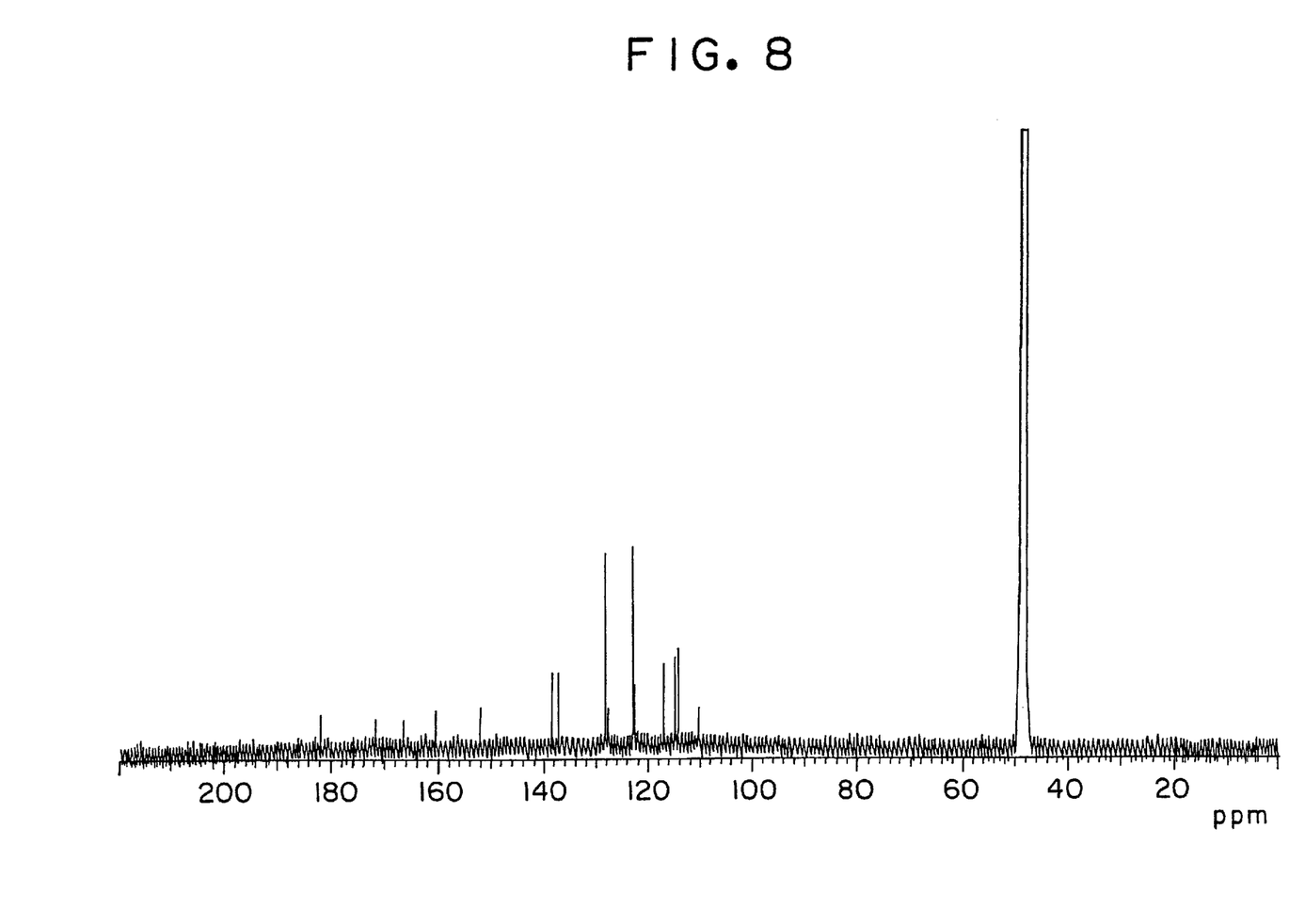
FIG. 8 shows carbon NMR spectrum of WK-5344B substance of the present invention (CD$_3$OD).

(10) Carbon NMR: FIG. 8 (Varian NMR, in dueterium methanol, 100 MHz)

Structure of WK-5344B substance was determined by considering the above physico-chemical properties and spectral data as follows.

After the reaction, 0.1% dextran sulfate 5 μl, 6 mM MgCl$_2$ 5 μl and 20 μl of phosphate buffer adjusted to ionic strength 0.16 were added therein and the mixture was allowed on ice for 20 minutes. The mixture was centrifuged at 4° C., 13000 rpm for 15 minutes. The precipitated LDL fraction was collected. LDL was dissolved in 0.1 N NaOH 180 μl and the transferred cholestryl ester in LDL was measured by liquid scintillation counter. Results of 50% inhibition for cholesteryl ester transfer protein activity were 0.54 μg/ml of WK-5344A substance and 2.0 μg/ml of WK-5344B substance.

As described hereinabove, WK-5344A substance and WK-5344B substance of the present invention show significant inhibitory action against cholesteryl ester transfer pro- As described hereinabove, physico-chemical properties of WK-5344A substance and WK-5344B substance were explained in details, no compounds identical with these properties have not been reported, and WK-5344A substance and WK-5344B substance are determined as novel substances.

Biological properties and inhibitory activity of WK-5344A substance and WK-5344B substance of the present invention are explained hereinbelow.

(1) Inhibitory Action for Human Cholestryl Ester Transfer Protein

Effect on cholesteryl ester transfer protein is determined using crude protein prepared from human plasma according to a method described in Kato, et al. Journal of Biological Chemistry, 264, 4082–4087, 1989.

Reconstructed high density lipoprotein (hereinafter designates as HDL) containing [1–$^{14}$C] cholesteryl ester 25 μl, human originated low density lipoprotein (hereinafter designates as LDL) 10 μl, 7 mM 5,5-dithiobisnitrobenzoic acid 30 μl, and partially purified human cholesteryl ester transfer protein 5 μl were combined. Total 150 μl reaction mixture was reacted at 37 ° C. for 30 minutes.

tein and are thought to be useful for prevention and treatment of diseases caused by accumulation of cholesterol in human.

DETAILED DESCRIPTION OF EMBODIMENTS OF THE INVENTION

Following example illustrates the present invention, but is not construed as limiting the present invention.

Example 100 ml of medium (adjusted to pH 7.0) containing starch 2.4% yeast extract 0.5%, glucose 0.1%, peptone 0.3%, meat extract 0.3% and $CaCO_3$ 0.4% in 500 ml Erlenmeyer flask, sealed with cotton plug, was steam sterilized. After cooling, a platinum loop of Streptomyces sp. Wk-5344 FERM BP-6668 grown on agar medium was inoculated aseptically thereto and shake cultured at 27° C. for 72 hours to obtain seed culture liquid.

A medium (adjusted to pH 6.5) containing soluble starch 4.0%, solvent extracted toasted soy bean meal 2.0%, 0.1N sodium thiosulfate 32 μl/l, $FeSO_4 \cdot 7H_2O$ 0.05%, $KH_2PO_4$ 0.05% and KCl 0.03% in 30 liter jar-fermenter was steam sterilized. After cooling, the seed culture liquid 200 ml was inoculated aseptically, and cultured with agitating at 250 rpm, aeration 10 liters/minute at 27° C. for 96 hours.

After cultivation, mycelia obtained by centrifugation of the cultured liquid were extracted with acetone 6 liters. The exctrat was concentrated in vacuo to remove acetone, adjusted to pH 5.0, extracted with ethyl acetate 10 liters, and concentrated the extract in vacuo to obtain crude substance 9.20 g. The crude substance was partitioned to hexane, methanol and water (40:19:1), collected the WK-5344 substance which was partitioned in the lower layer, and concentrated in vacuo to obtain crude substance 1.29 g. The crude substance was suspended in acetonitrile 10 ml, charged on column of ODS (20 ml, Senshu Co., SSC-ODS-7515-12), and chromatographed with elution with acetonitrile containing 0.05% phosphoric acid.

Eluate 12 ml fraction was collected, and the fractions containing active ingredient were collected. After removing acetonitrile, aqueous layer fraction was extracted with ethyl acetate and dried in vacuo to obtain crude active substance 157 mg.

The crude active substance 157 mg was dissolved in methanol 1.57 ml, charged on a column of ODS (147 ml, Senshu Co., SSC-ODS-7515-12), and chromatographed with stepwise elution with acetonitrile containing 0.05% phosphoric acid. Eluate 12 ml fraction was collected, and the fractions containing active ingredient were collected. After removing acetonitrile, aqueous layer fraction was extracted with ethyl acetate and dried in vacuo to obtain crude active substance 19.5 mg.

The crude active substance 19.5 mg was dissolved in chloroform 0.5 ml, charged on a column of silica gel (126 ml, Kiesel gel 60), and chromatographed with elution with chloroform and methanol. Each fraction was fractionated with 12 ml. As a result, WK-5344A substance 1.69 mg and WK-5344B substance 1.12 mg were isolated.

EFFECT OF THE INVENTION

As described hereinabove, a microorganism belonging to genus Streptomyces having ability to produce WK-5344A substance and WK-5344B substance was cultured in a medium to accumulate WK-5344A substance and WK-5344B substance in the cultured mass. The WK-5344A substance and WK-5344B substance were collected from said cultured mass to obtain substances having inhibitory action on cholesteryl ester transfer protein. Said substances are expected to show preventive and curative effects for adult diseases such as myocardial infarction and cerebral accident caused by arterial sclerosis.

What is claimed is:

1. WK-5344A substance represented by the following formula or salt thereof.

2. WK-5344B substance represented by the following formula or salt thereof.

3. A process for production of WK-5344A substance and WK-5344B substance or pharmaceutically acceptable salt thereof comprising culturing a microorganism belonging to genus Streptomyces and having ability to produce WK-5344A substance and WK-5344B substance in a medium, accumulating the WK-5344A substance and the WK-5344B substance in a cultured medium, and isolating the WK-5344A substance and the WK-5344B substance from the cultured medium, and if required said substances are converted to pharmaceutically acceptable salt thereof.

4. The process according to claim 3 wherein the microorganism belonging to genus Streptomyces and having ability to produce the WK-5344A substance and the WK-5344B substance is Streptomyces sp. WK-5344.

5. An isolated microorganism belonging to genus Streptomyces and having ability to produce WK-5344A substance and WK-5344B substance wherein the microorganism is Streptomyces sp. WK-5344 FERM BP-6668.

* * * * *